United States Patent
Ring et al.

(10) Patent No.: US 9,327,074 B2
(45) Date of Patent: May 3, 2016

(54) IMPLANTABLE INFUSION DEVICES INCLUDING APPARATUS FOR CONFIRMING FLUID FLOW AND SYSTEMS, APPARATUS AND METHODS ASSOCIATED WITH SAME

(71) Applicant: The Alfred E. Mann Foundation For Scientific Research, Santa Clarita, CA (US)

(72) Inventors: Lawrence Scott Ring, Valencia, CA (US); Peter C. Lord, Kihei, HI (US); Scott R. Gibson, Granada Hills, CA (US); Sam W. Bowman, Valencia, CA (US); Brian M. Shelton, Pasadena, CA (US)

(73) Assignee: Medallion Therapeutics, Inc., Valencia, CA (US)

( * ) Notice: Subject to any disclaimer, the term of this patent is extended or adjusted under 35 U.S.C. 154(b) by 531 days.

(21) Appl. No.: 13/676,738

(22) Filed: Nov. 14, 2012

(65) Prior Publication Data
US 2013/0197487 A1 Aug. 1, 2013

Related U.S. Application Data

(63) Continuation of application No. 12/329,459, filed on Dec. 5, 2008, now Pat. No. 8,323,268.

(60) Provisional application No. 60/992,979, filed on Dec. 6, 2007.

(51) Int. Cl.
*A61M 5/142* (2006.01)
*A61M 5/168* (2006.01)
*G01F 1/28* (2006.01)

(52) U.S. Cl.
CPC ....... *A61M 5/16886* (2013.01); *A61M 5/14276* (2013.01); *A61M 5/16854* (2013.01); *G01F 1/28* (2013.01); *A61M 2205/0244* (2013.01); *A61M 2205/0294* (2013.01); *A61M 2205/3523* (2013.01)

(58) Field of Classification Search
CPC .................. A61M 5/14276; A61M 2205/3523; A61M 5/16854; A61M 2205/0244; A61M 2205/0294; A61M 5/16886
See application file for complete search history.

(56) References Cited

U.S. PATENT DOCUMENTS

| | | | |
|---|---|---|---|
| 5,663,508 | A | 9/1997 | Sparks |
| 7,320,676 | B2 | 1/2008 | Miesel |
| 8,323,268 | B2 | 12/2012 | Ring et al. |
| 2003/0135154 | A1 | 7/2003 | Heiniger et al. |
| 2005/0075624 | A1 | 4/2005 | Miesel |
| 2005/0104457 | A1 | 5/2005 | Jordan et al. |
| 2005/0273014 | A1 | 12/2005 | Gianchandani et al. |
| 2006/0184119 | A1 | 8/2006 | Remde et al. |
| 2006/0212096 | A1 | 9/2006 | Stevenson |
| 2007/0106152 | A1 | 5/2007 | Kantrowitz et al. |
| 2007/0142728 | A1 | 6/2007 | Penner et al. |
| 2008/0009837 | A1 | 1/2008 | Miesel |
| 2008/0129486 | A1 | 6/2008 | Jeckelmann et al. |

(Continued)

FOREIGN PATENT DOCUMENTS

WO WO 2007/002084 1/2007

*Primary Examiner* — Aarti B Berdichevsky
(74) *Attorney, Agent, or Firm* — Henricks, Slavin, Holmes LLP

(57) ABSTRACT

Implantable infusion apparatus, systems and methods that involve the use of a sensor that is associated with the catheter outlet.

22 Claims, 7 Drawing Sheets

(56) References Cited

U.S. PATENT DOCUMENTS

| | | |
|---|---|---|
| 2008/0300572 A1 | 12/2008 | Rankers et al. |
| 2008/0306466 A1 | 12/2008 | Shelton et al. |
| 2009/0082758 A1 | 3/2009 | Gill et al. |
| 2009/0115406 A1 | 5/2009 | Anderson et al. |
| 2009/0119124 A1 | 5/2009 | Kambaloor |
| 2009/0243943 A1 | 10/2009 | Mumbru et al. |
| 2009/0306632 A1 | 12/2009 | Trovato et al. |
| 2009/0306633 A1 | 12/2009 | Trovato et al. |
| 2010/0022992 A1 | 1/2010 | Genosar et al. |
| 2010/0069841 A1 | 3/2010 | Miesel |

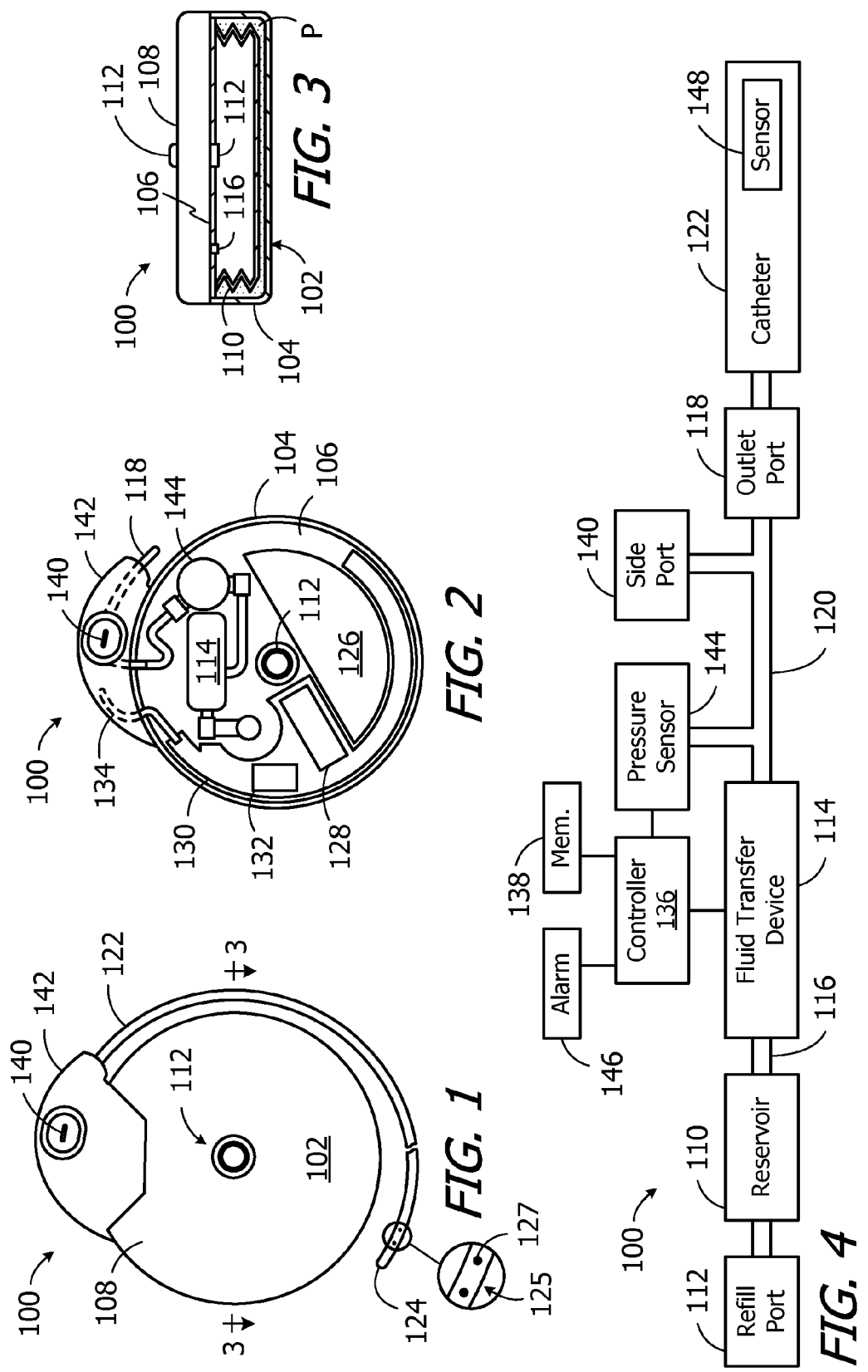

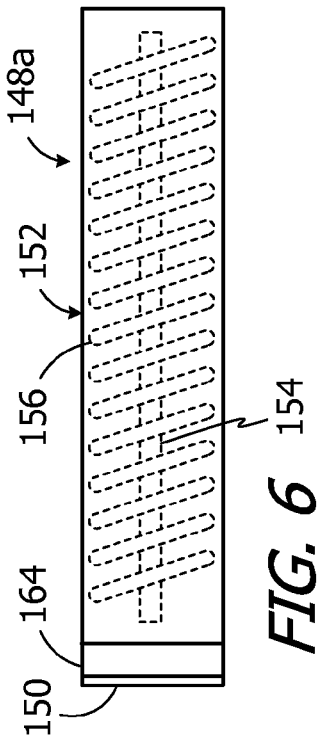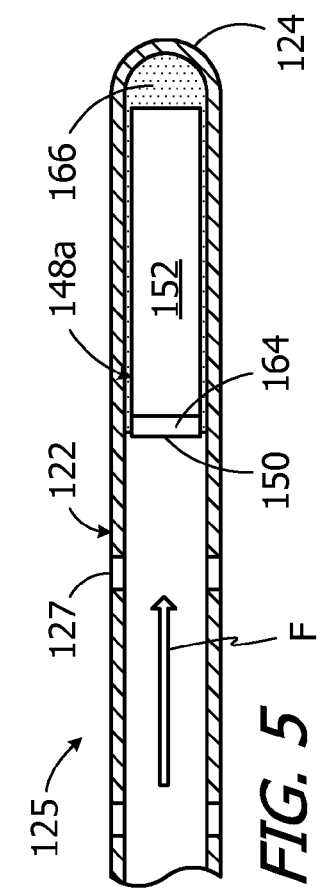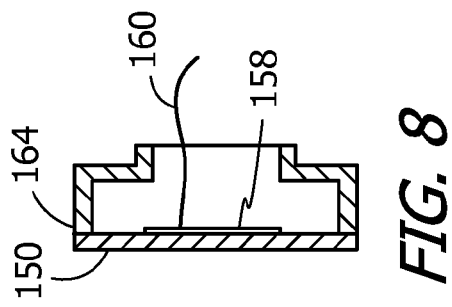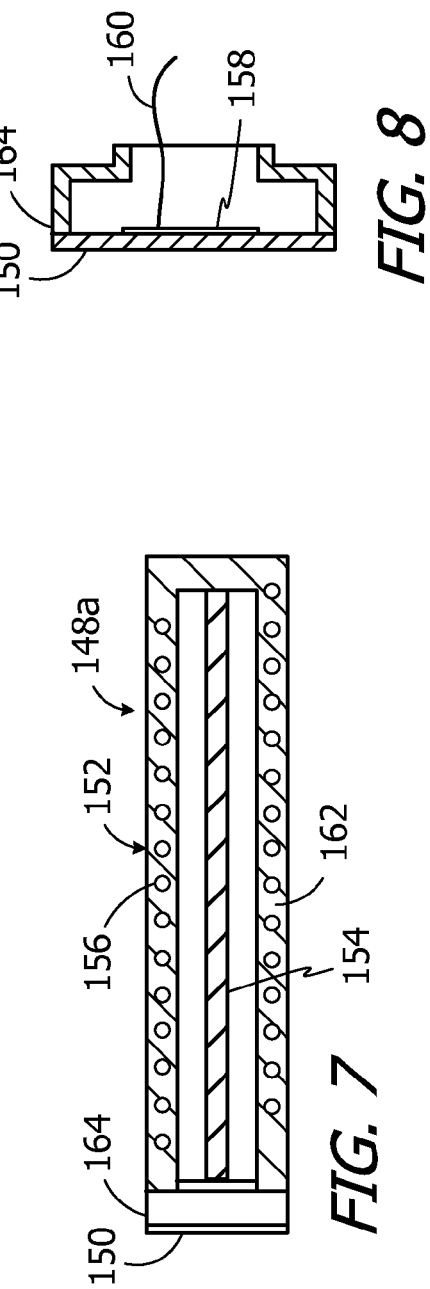

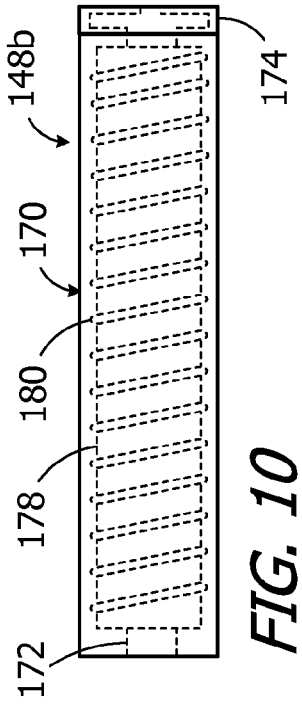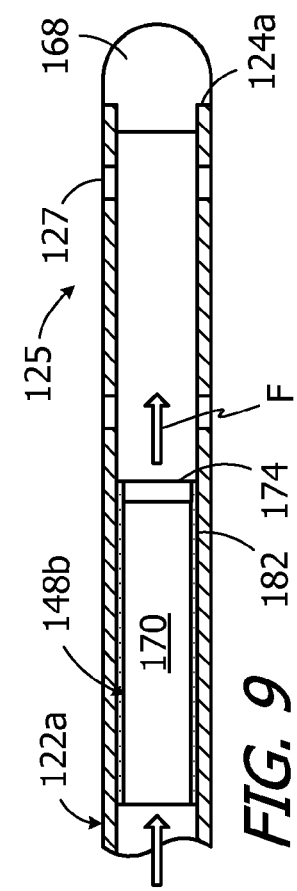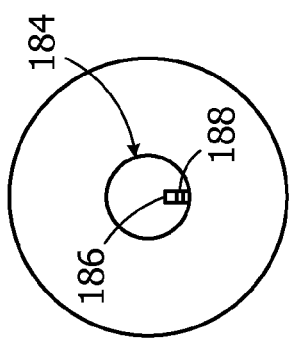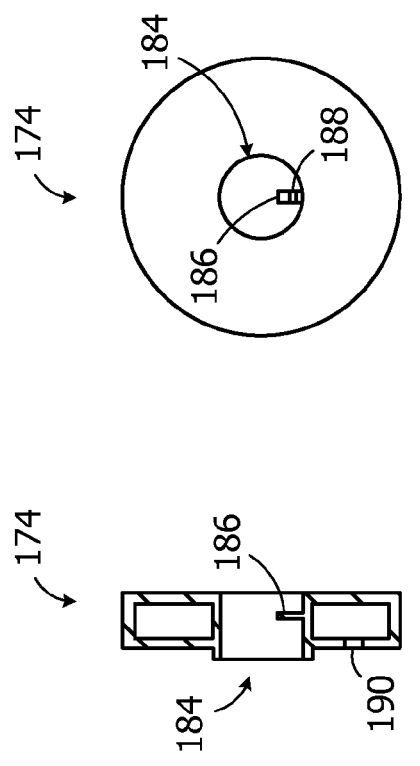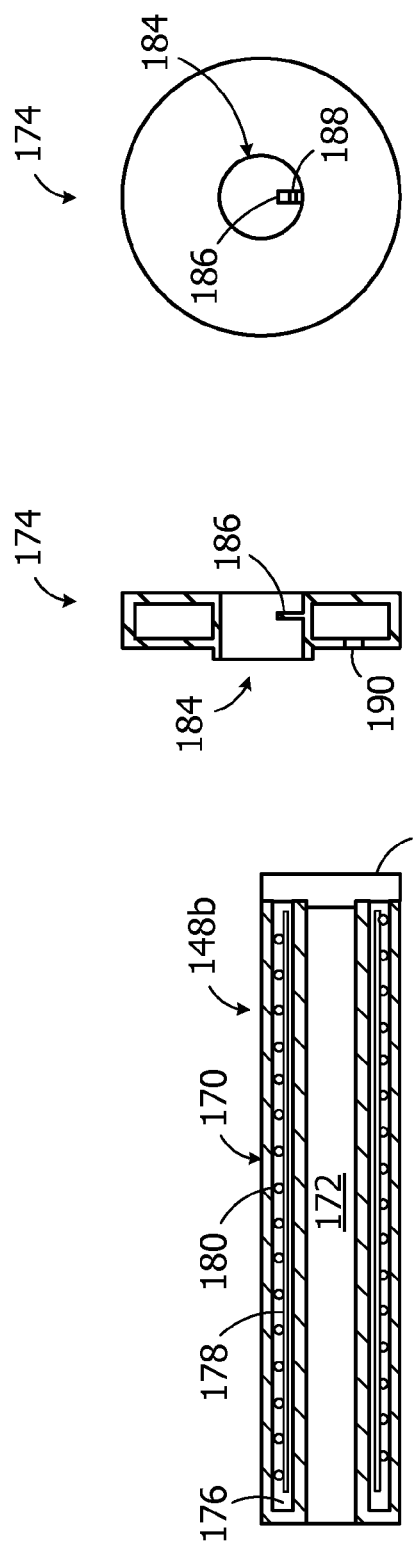

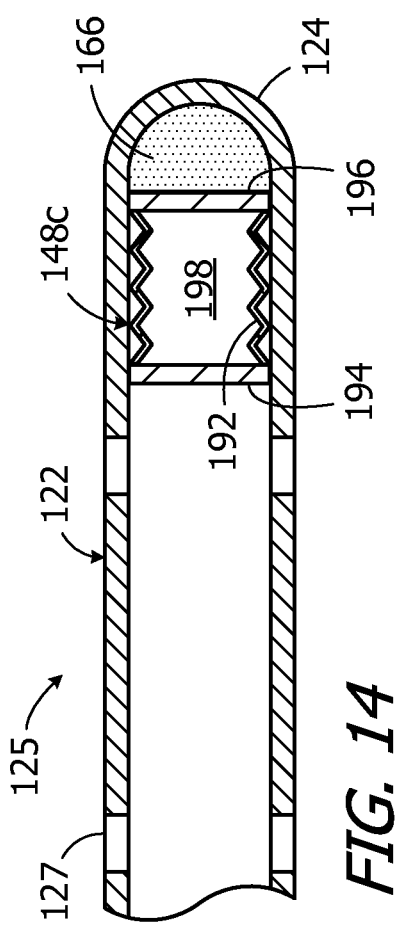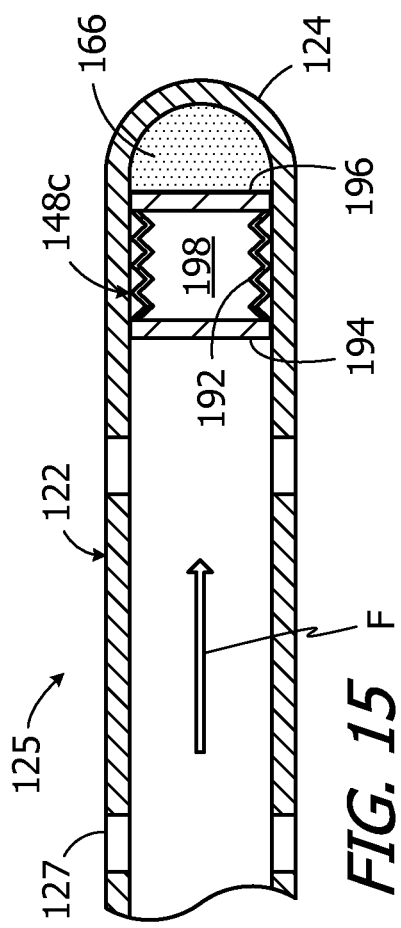

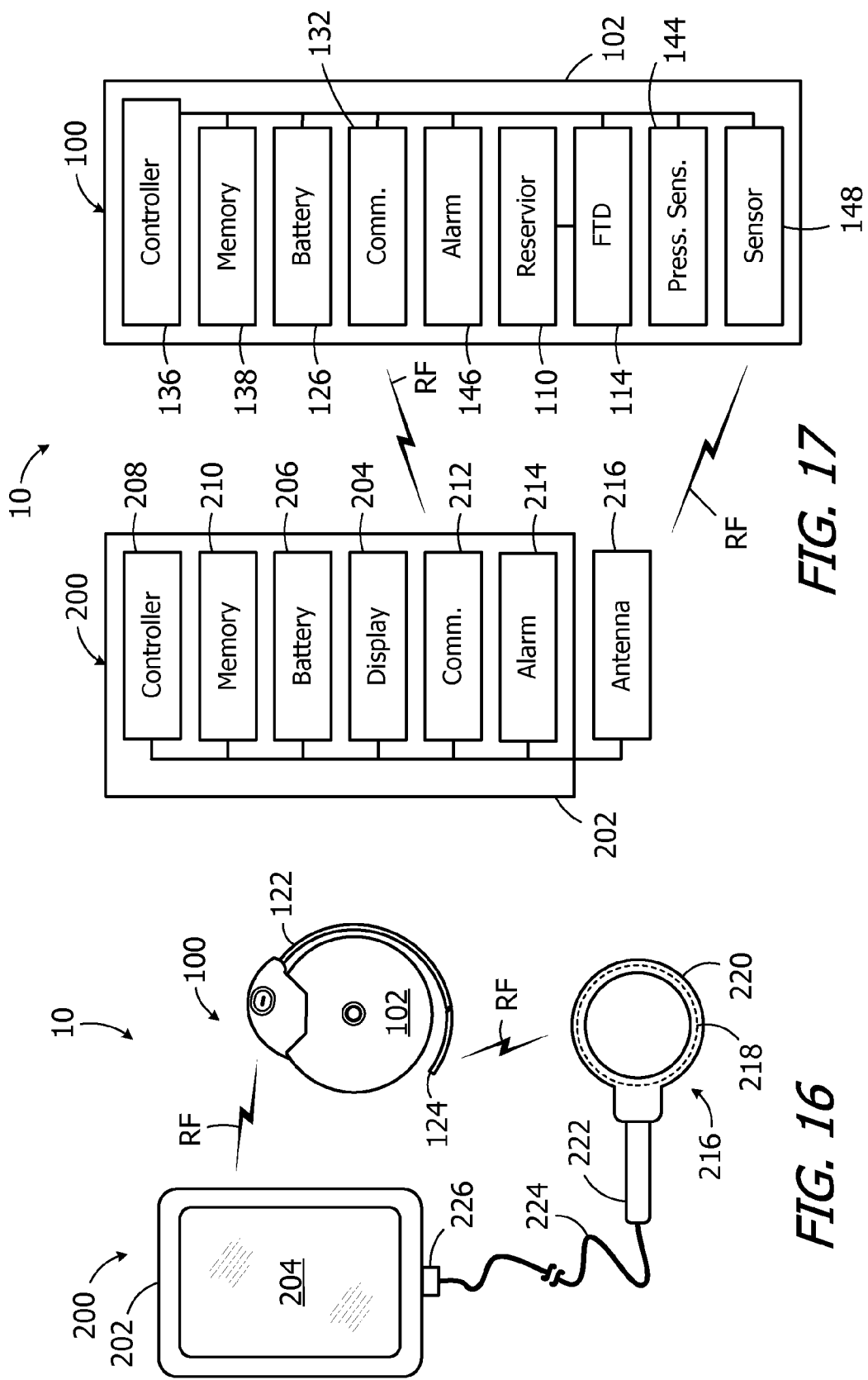

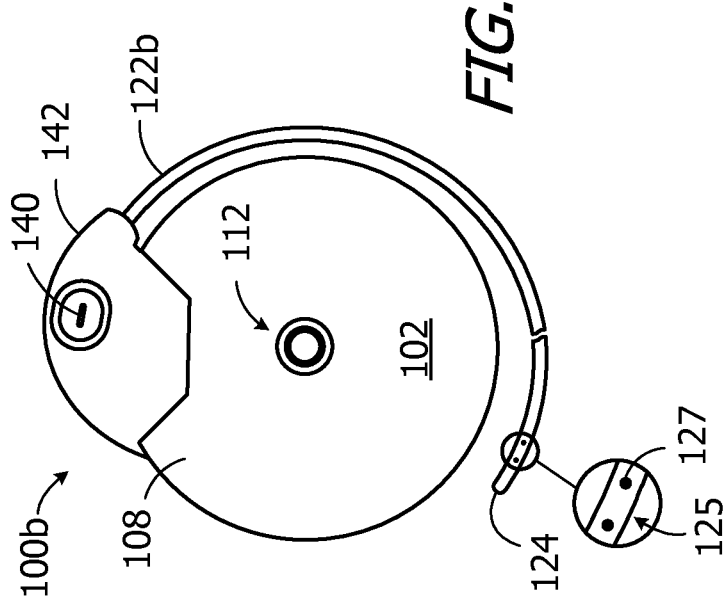
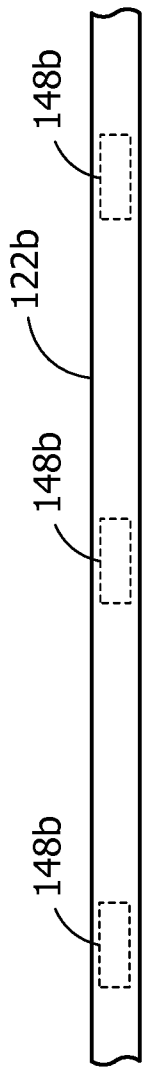

IMPLANTABLE INFUSION DEVICES INCLUDING APPARATUS FOR CONFIRMING FLUID FLOW AND SYSTEMS, APPARATUS AND METHODS ASSOCIATED WITH SAME

CROSS-REFERENCE TO RELATED APPLICATION

This application is a continuation of application Ser. No. 12/329,459, filed Dec. 5, 2008, now U.S. Pat. No. 8,323,268, which claims the benefit of U.S. Provisional Application Ser. No. 60/992,979, filed Dec. 6, 2007 and entitled "Implantable Infusion Devices Including Apparatus For Confirming Fluid Flow And Systems, Apparatus And Methods Associated With Same," which is incorporated herein by reference in its entirety.

BACKGROUND OF THE INVENTIONS

1. Field of Inventions

The present inventions relate generally to implantable infusion devices.

2. Description of the Related Art

Implantable infusion devices have been used to provide patients with a medication or other substance (collectively "infusible substance") and frequently include a reservoir and a fluid transfer device. The reservoir is used to store the infusible substance and, in some instances, implantable infusion devices are provided with a refill port that allows the reservoir to be transcutaneously filled (and/or re-filled) with a hypodermic needle. The reservoir is coupled to the fluid transfer device, which is in turn connected to an outlet port. A catheter, which has an outlet at the target body region, may be connected to the outlet port. As such, infusible substance from the reservoir may be transferred from the reservoir to the target body region by way of the fluid transfer device and catheter.

One issue associated with implantable infusion devices involves situations where the patient informs the clinician that the therapy provided by the implantable infusion device is not, or is no longer, effective. For example, a patient in which pain medication is being delivered to a particular location within the intrathecal space may complain of back pain if the therapy provided by the implantable infusion device is no longer effective. In order to properly adjust the therapy, the clinician must be able to determine whether the source of the problem is infusible substance related (e.g. the patient has built up a resistance to the medication) or implantable infusion device related (e.g. there is catheter blockage, leak or disconnect, or the fluid transfer device has failed, or the reservoir is empty). Given the fact that the pump and catheter are implanted within the patient, the "infusible substance or infusion device" determination can be difficult, time consuming and invasive.

Accordingly, the present inventors have determined it would be desirable to provide the clinician with an efficient way to determine whether the infusible substance or the implantable medical device is the source of the therapeutic shortcoming.

SUMMARY OF THE INVENTIONS

The present apparatus and methods involve the use of one or more sensor devices that are associated with the catheter and may be queried as necessary to determine whether or not there is infusible substance flow through the catheter. In at least some implementations, the sensor device is capable of wireless communication with an external device, such as a clinician's programming unit, and is not powered by the implantable medical device power supply.

There are a variety of advantages associated with such a sensor device. For example, the lack of infusible substance flow through the catheter outlet is indicative of a failure that is associated with the implantable infusion device, such as a blocked catheter, a catheter leak, a disconnected catheter, a pump mechanism failure, or an empty reservoir. Accordingly, allowing the clinician to wirelessly contact the sensor device and determine whether fluid is flowing from the outlet makes it much easier to determine whether a particular therapeutic shortcoming is infusible substance related or infusion device related. The sensor device may also be used to identify the location of the catheter outlet, which advantageously allows the clinician to identify those instances where an otherwise properly functioning implantable medical device is not delivering the infusible substance to the proper location.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of exemplary embodiments will be made with reference to the accompanying drawings.

FIG. 1 is a plan view of an implantable infusion device in accordance with one embodiment of a present invention.

FIG. 2 is a plan view of the implantable infusion device illustrated in FIG. 1 with the cover removed.

FIG. 3 is a partial section view taken along line 3-3 in FIG. 1.

FIG. 4 is a block diagram of the implantable infusion device illustrated in FIGS. 1-3.

FIG. 5 is a side, partial section view of a catheter and a sensor device in accordance with one embodiment of a present invention.

FIG. 6 is a side view of the sensor device illustrated in FIG. 5.

FIG. 7 is a side, partial section view of the sensor device illustrated in FIG. 5.

FIG. 8 is a section view of a portion of the sensor device illustrated in FIG. 5.

FIG. 9 is a side, partial section view of a catheter and a sensor device in accordance with one embodiment of a present invention.

FIG. 10 is a side view of the sensor device illustrated in FIG. 9.

FIG. 11 is a side, partial section view of the sensor device illustrated in FIG. 9.

FIG. 12 is a section view of a portion of the sensor device illustrated in FIG. 9.

FIG. 13 is an end view of the sensor device illustrated in FIG. 9.

FIG. 14 is a side, partial section view of a catheter and a sensor device in accordance with one embodiment of a present invention.

FIG. 15 is another side, partial section view of the catheter and sensor device illustrated in FIG. 14.

FIG. 16 is a plan view of an implantable infusion device system in accordance with one embodiment of a present invention.

FIG. 17 is a block diagram of the implantable infusion device system illustrated in FIG. 16.

FIG. 19 is a plan view of an implantable infusion device in accordance with one embodiment of a present invention.

FIG. 20 is a side view of a portion of the catheter illustrated in FIG. 19.

DETAILED DESCRIPTION OF THE EXEMPLARY EMBODIMENTS

Figure 18:
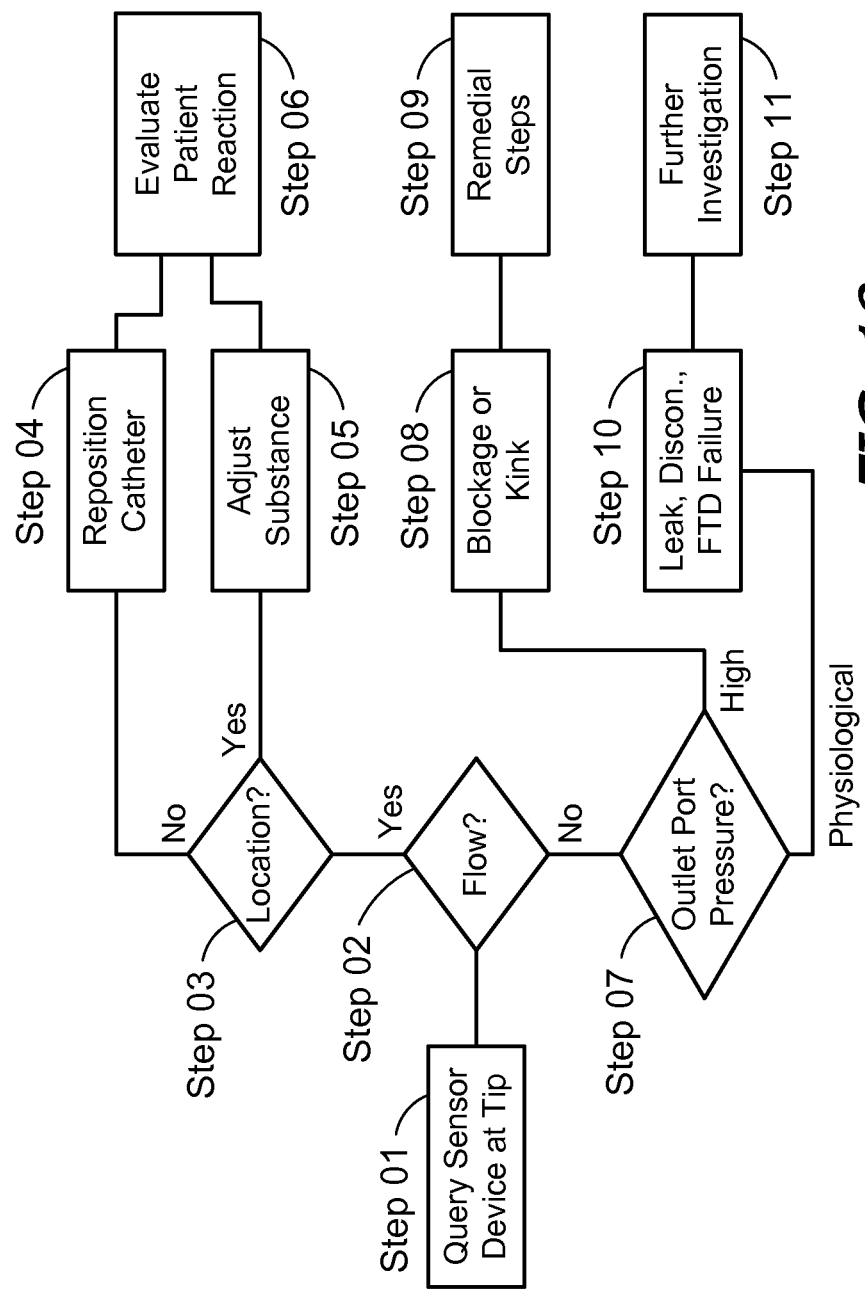
FIG. 18 is a flow chart showing a process in accordance with one embodiment of a present invention.

The following is a detailed description of the best presently known modes of carrying out the inventions. This description is not to be taken in a limiting sense, but is made merely for the purpose of illustrating the general principles of the inventions. The present inventions are also not limited to the exemplary implantable infusion device described herein and, instead, are applicable to other implantable infusion devices that currently exist or are yet to be developed.

One example of an implantable infusion device in accordance with a present invention is generally represented by reference numeral 100 in FIGS. 1-4. As used herein, an "implantable infusion device" is a device that includes a reservoir and an outlet, and is sized, shaped and otherwise constructed (e.g. sealed) such that both the reservoir and outlet can be simultaneously carried within the patient's body. The exemplary infusion device 100 includes a housing 102 (e.g. a titanium housing) with a bottom portion 104, an internal wall 106, and a cover 108. An infusible substance (e.g. medication) may be stored in a reservoir 110 that is located within the housing bottom portion 104. The reservoir 110 may be replenished by way of a refill port 112 that extends from the reservoir, through the internal wall 106, to the cover 108. A hypodermic needle (not shown), which is configured to be pushed through the refill port 112, may be used to replenish the reservoir 110.

A wide variety of reservoirs may be employed. In the illustrated embodiment, the reservoir 110 is in the form of a titanium bellows that is positioned within a sealed volume defined by the housing bottom portion 104 and internal wall 106. The remainder of the sealed volume is occupied by propellant P, which may be used to exert negative pressure on the reservoir 110. Other reservoirs that may be employed in the present infusion devices include reservoirs in which propellant exerts a positive pressure. Still other exemplary reservoirs include negative pressure reservoirs that employ a movable wall that is exposed to ambient pressure and is configured to exert a force that produces an interior pressure which is always negative with respect to the ambient pressure.

The exemplary ambulatory infusion device 100 illustrated in FIGS. 1-4 also includes a fluid transfer device 114. The inlet of a fluid transfer device 114 is coupled to the interior of the reservoir 110 by a passageway 116, while the outlet of the fluid transfer device is coupled to an outlet port 118 by a passageway 120. Operation of the fluid transfer device 114 causes infusible substance to move from the reservoir 110 to the outlet port 118. A catheter 122 may be connected to the outlet port 118 so that the infusible substance passing through the outlet port will be delivered to a target body region in spaced relation to the infusion device 100 by way of an outlet at or near the catheter end 124. The outlet may, for example, be an opening at the catheter end 124. Alternatively, in the illustrated embodiments, the outlet 125 (FIG. 1) is in the form of a plurality of apertures 127 that are located near the catheter end 124.

A wide variety of fluid transfer devices may be employed. In the illustrated embodiment, the fluid transfer device 114 is in the form of an electromagnet pump. The present inventions are not, however, limited to electromagnet pumps and may include other types of fluid transfer devices. Such devices include, but are not limited to, other electromagnetic pumps, solenoid pumps, piezo pumps, and any other mechanical or electromechanical pulsatile pump. In the exemplary context of implantable drug delivery devices, and although the volume/stroke magnitude may be increased in certain situations, the fluid transfer devices will typically deliver about 1 microliter/stroke, but may be more or less depending on the particular fluid transfer device employed. Additionally, although the exemplary fluid transfer device 114 is provided with internal valves (e.g. a main check valve and a bypass valve), valves may also be provided as separate structural elements that are positioned upstream of and/or downstream from the associated fluid transfer device.

Energy for the fluid transfer device 114, as well for other aspects of the exemplary infusion device 100, is provided by the battery 126 illustrated in FIG. 2. In the specific case of the fluid transfer device 114, the battery 126 is used to charge one or more capacitors 128, and is not directly connected to the fluid transfer device itself. The capacitor(s) 128 are connected to an electromagnet coil in the fluid transfer device 114, and disconnected from the battery 126, when the electromagnet coil is being energized, and are disconnected from the electromagnet coil and connected to the battery when the capacitor(s) are being recharged and/or when the fluid transfer device is at rest. The capacitor(s) 128 are carried on a board 130. A communication device 132, which is connected to an antenna 134, is carried on the same side of the board 130 as the capacitor(s) 128. The exemplary communication device 132 is an RF communication device. Other suitable communication devices include, but are not limited to, oscillating magnetic field communication devices, static magnetic field communication devices, optical communication devices, ultrasound communication devices and direct electrical communication devices.

A controller 136 (FIG. 4), such as a microprocessor, microcontroller or other control circuitry, is carried on the other side of the board 130. The controller controls the operations of the infusion device 100 in accordance with instructions stored in memory 138 and/or provided by an external device, e.g. the clinician's programming unit 200 described below with reference to FIGS. 16 and 17 or a patient's remote control (not shown) by way of the communication device 132. For example, the controller 136 may be used to control the fluid transfer device 114 to supply fluid to the patient in accordance with, for example, a stored basal delivery schedule or a bolus delivery request.

Referring to FIGS. 1, 2 and 4, the exemplary infusion device 100 is also provided with a side port 140 that is connected to the passageway 120 between the outlet of the fluid transfer device 114 and the outlet port 118. The side port 140 facilitates access to an implanted catheter 122, typically by way of a hypodermic needle. For example, the side port 140 allows clinicians to push fluid into the catheter 122 and/or draw fluid from the catheter for purposes such as checking catheter patency, sampling CSF, injecting contrast dye into the patient and/or catheter, removing medication from the catheter prior to dye injection, injecting additional medication into the region at the catheter outlet 125, and/or removing pharmaceuticals or other fluids that are causing an allergic or otherwise undesirable biologic reaction.

The outlet port 118, a portion of the passageway 120, the antenna 134 and the side port 140 are carried by a header assembly 142. The header assembly 142 is typically a molded, plastic structure that is secured to the housing 102. The housing 102 includes a small aperture through which portions of the passageway 120 are connected to one another, and a small aperture through which the antenna 134 is connected to the board 130.

The exemplary infusion device 100 illustrated in FIGS. 1-4 may include a pressure sensor 144 that is connected to the passageway 120 between the outlet of the fluid transfer device 114 and the outlet port 118. As such, the pressure sensor 144 senses the pressure at the outlet port 118. The pressure sensor 144 is connected to the controller 136 and may be used to analyze a variety of aspects of the operation of the exemplary implantable infusion device 100. For example, pressure measurements may be used to determine whether or not the fluid transfer device 114 is functioning properly. The controller 136 may perform a variety of different functions in response to determination that the fluid transfer device 114 is not functioning properly. For example, the controller 136 may actuate an audible alarm 146 that is located within the housing 102 in order to signal that the fluid transfer device 114 is not functioning properly. Other uses for the pressure sensor 144 are described below.

The exemplary infusion device 100 also includes a sensor device 148 at or near the catheter end 124 that is configured to measure a characteristic which is indicative of fluid flow through the catheter outlet 125 ("fluid flow characteristic"). Suitable fluid flow characteristics include, but are not limited to, the flow rate within the catheter 122 at or near the catheter outlet 125 and the pressure within the catheter at or near the catheter outlet. Fluid flow at the expected rate at or near the catheter outlet 125 is, of course, a direct indication that the fluid transfer device 114 is operating properly, that the catheter 122 is properly connected, that there are no leaks in the catheter, that the outlet 125 is not blocked, and that the intended volume of fluid is flowing from outlet 125. Conversely, when the flow rate is below the expected rate (including no flow at all), it may be assumed that the fluid transfer device 114 is not operating properly, and/or that the catheter 122 is disconnected, and/or that there is a leak in the catheter, and/or that the outlet 125 is blocked.

Turning to pressure within the catheter 122, when the infusion device 100 is operating properly and there is no catheter blockage or disconnect, the pressure within the catheter will be equal to the internal body pressure ("physiological pressure") between operations of the fluid transfer device 114. Operations of the fluid transfer device 114 (e.g. a pump strokes) result in positive pressure events (sometimes referred to as "artifacts"), which are a brief increase in the catheter pressure. Each increase in catheter pressure is followed by a return to physiological pressure. Accordingly, when the sensor device 148 senses a positive pressure event of the expected magnitude at or near the catheter outlet 125 followed by a return to physiological pressure, it may be assumed that the fluid transfer device 114 is operating properly, that the catheter 122 is properly connected, that there are no leaks in the catheter, that the outlet is not blocked, and that fluid is flowing from outlet 125.

The lack of a sensed positive pressure event and/or a return to physiological pressure thereafter is indicative of a problem associated with the infusion device 100. More specifically, if a positive pressure event is not sensed by the sensor device 148, it may be assumed that the fluid transfer device 114 is not operating properly, and/or that the catheter 122 is disconnected, and/or that there is leak in the catheter, and/or that the outlet 125 has been blocked long enough for the pressure within the catheter to reach the "dead end" pressure. If positive pressure events are sensed by the sensor device 148, but the sensed pressure does not return to physiological pressure and, instead, increases with each operation of the fluid transfer device 114, it may be assumed that the outlet 125 is blocked and that the "dead end" pressure has not been reached.

It should also be noted here that the catheter 122 may be configured so as to increase the fidelity of the positive pressure event measurements. In particular, the catheter 122 could be relatively stiff and/or have a relatively small lumen. The positive pressure events may also be analyzed more closely. For example, pressure v. time waveforms of the positive pressure events may be analyzed, as opposed to simply analyzing a single pressure measurement taken during a positive pressure event or the average of a number of pressure measurements taken during the positive pressure event.

The sensor device 148 may be configured such that it is capable of wireless communication generally, and wireless communication of data that is representative of a fluid flow characteristic in particular. Such communication may be with a device that is located outside the patient's body (e.g. a clinician's programming unit or a patient's remote control). As discussed in greater detail below, once outside the patient's body, the fluid flow characteristic data may be used to determine whether the source of a therapeutic failure is infusible substance related or implantable infusion device related. The sensor device 148 is also configured such that it need not be powered, either directly or indirectly, by the battery 126 or other power source within the implantable infusion device 100. When so configured, the sensor device 148 is not an additional load on the battery 126 or other power source. The sensor device 148 in the illustrated exemplary embodiment is also not connected to structures within the housing 102 (e.g. the battery 126, board 130 or the controller 136) by a cable, wire or other electrical connection, which simplifies the manufacturing process.

With respect to the particular configuration of the sensor device 148, a wide variety of sensor devices may be employed. Although the present inventions are not limited to any particular configuration, one exemplary sensor device is generally represented by reference numeral 148a in FIGS. 5-8. The sensor device 148a is a pressure sensor device that measures fluid pressure within the catheter 122 at or near the catheter outlet 125. To that end, the exemplary pressure sensor device 148a includes a pressure responsive element (e.g. a diaphragm) 150, a housing 152, a circuit board 154 within the housing, and an inductive coil 156. The inner surface of the pressure responsive element 150, which faces upstream against the fluid flow F, includes a strain gauge 158 (FIG. 8) that is connected to the circuit board 154 by a multi-wire wire cable 160. Alternatively, the circuit board 154 may include a light source and light sensor arrangement that measures deflection of the pressure responsive element 150. The housing 152 in the illustrated embodiment is formed from ceramic and includes an open end, a closed end and a cylindrical wall 162 therebetween. The exemplary inductive coil 156 may be embedded within the cylindrical wall 162 but for its connection to the circuit board 154, as shown, or positioned along the inner surface of the cylindrical wall. The pressure responsive element 150 is carried by a metal cap 164 that is secured to the open end of the housing 152 (e.g. by brazing) to hermetically seal the interior of the housing.

During assembly, the pressure sensor device 148a may be inserted into the catheter end 124, which is open prior to assembly, and secured in place with adhesive 166. The catheter end 124 may then be thermal formed into the closed curved shape shown in FIG. 5. Suitable adhesives include, but are not limited to, relatively soft adhesives such as silicone adhesive which results in soft, atraumatic tip. Radiopaque powder may be added to the adhesive 166 in order to insure that the catheter end 124 can be observed with a fluoroscope or the like.

The exemplary sensor device 148a illustrated in FIGS. 5-8 may be powered in a variety of ways. In the exemplary implementation, the sensor device is a "passive" device that is directly powered by way of an inductive coupling to an external power source, e.g. is powered by a query from the clinician's programming unit 200 (FIGS. 16 and 17) or a patient's remote control (not shown), and is only operable during inductive power transfer. The sensor device 148a may, however, be a "semi-passive" device that includes a battery, capacitor or other energy storage device that is charged during the inductive coupling, thereby allowing the sensor device to operate for a short time after the inductive power transfer ends. The sensor device 148a may also be an "active" device that includes its own energy source.

The exemplary sensor device 148a will, as noted above, provide data concerning the fluid pressure within the catheter 122 at or near the catheter outlet 125 in response to a query from an interrogating device such as the clinician's programming unit 200 (FIGS. 16 and 17) or a patient's remote control (not shown). More specifically, when inductively coupled to and powered by the interrogating device by way of the coil 156, the circuitry on the circuit board 154 will use the strain gauge 158 to measure the deflection of the pressure responsive element 150, which is indicative of the pressure within the catheter 122. The circuitry on the circuit board 154 then calculates the pressure and transmits pressure data to the interrogating device by way of the coil 156. Alternatively, the transmitted data may simply be deflection or strain data and the interrogating device may be used to perform the pressure calculations.

It should be noted here that the interrogating device could time the query such that it corresponds to the periodic operation of the fluid transfer device 114. For example, if the implantable infusion device 100 is programmed such that the fluid transfer device 114 only operates for a few seconds at the beginning of each minute, then the interrogating device could synchronize itself with the implantable infusion device 100 and only send out queries during the few seconds at the beginning of each minute.

Turning to FIGS. 9-13, implantable infusion devices in accordance with other implementations may include the catheter 122a and/or the sensor device 148b. The exemplary catheter 122a is substantially similar to catheter 122. Here, however, the catheter end 124a is not formed into a closed curve. A titanium tip 168, which is radiopaque, is mounted on the open catheter end 124a instead. The fluid outlet 125 (defined by apertures 127) is also closer to the end of the catheter. Turning to sensing, the sensor device 148b is a flow sensor device that measures fluid flow within the catheter 122a at or near the catheter outlet 125. Such flow is indicative of flow through the outlet 125.

The exemplary flow sensor device 148b includes a ceramic housing 170 with an inner lumen 172 for fluid flow and a flow sensor 174 mounted on the housing at one end of the inner lumen. The housing 170 also includes an annular compartment 176 (FIG. 11) for a cylindrical circuit board 178 which carries circuitry (not shown) on one side and an inductive coil 180 on the other. Adhesive 182, which may include radiopaque powder, secures the sensor device 148b to the inner surface of the catheter 122a.

A wide variety of flow sensors may be employed and, in the illustrated embodiment, the flow sensor 174 is an electromechanical flow sensor. Other suitable sensors include, but are not limited to, thermal dilution sensors and ultrasonic particle detection sensors. Referring more specifically to FIGS. 11-13, the exemplary flow sensor 174 is a micromachined silicon structure that includes a fluid lumen 184 and a deflectable cantilevered beam 186. A strain element 188 (FIG. 13) is carried by the cantilevered beam 186 and is connected to the circuit board 178 by suitable wiring (not shown) that extends through an opening 190. The flow sensor 174 is also secured to the end of the housing 170 (e.g. by brazing) to hermetically seal the annular compartment 176. Additional details concerning this type of flow sensor may be found in, for example, U.S. Pat. No. 5,663,508.

The exemplary sensor device 148b illustrated in FIGS. 9-13 may be powered in a variety of ways. In the exemplary implementation, the sensor device is a "passive" device that is directly powered by way of an inductive coupling to an external power source, e.g. during a query from the clinician's programming unit 200 (FIGS. 16 and 17) or a patient's remote control (not shown), and is only operable during the inductive power transfer. The sensor device 148b may, however, be a "semi-passive" device that includes a battery, capacitor or other energy storage device that is charged during the inductive coupling, thereby allowing the sensor device to operate for a short time after the inductive power transfer ends. The sensor device 148a may also be an "active" device that includes its own energy source.

The exemplary sensor device 148b will provide data concerning the rate of fluid flow within the catheter 122a at or near the catheter outlet 125 in response to a query from an interrogating device, such as the clinician's programming unit 200 (FIGS. 16 and 17) or a patient's remote control (not shown). More specifically, when inductively coupled to and powered by the interrogating device by way of the coil 180, the circuitry on the circuit board 178 will use the strain element 188 to measure the deflection of the cantilevered beam 186, which is indicative of the flow within the catheter 122a. The circuitry on the circuit board 178 calculates the flow rate and transmits flow rate data to the interrogating device by the coil 180. Alternatively, the transmitted data may simply be deflection or strain data and the interrogating device may be used to perform the pressure calculations.

The flow rate, deflection or strain data may be analyzed in a variety of ways. For example, a single flow rate, deflection or strain data point, or an average of a number of data points, associated with each fluid transfer device actuation may be analyzed. Alternatively, a data v. time waveform associated with each fluid transfer device actuation may be analyzed.

Implantable infusion devices in accordance with other implementations may include the sensor device 148c illustrated in FIGS. 14 and 15. The sensor device 148c, which is a pressure sensor device that measures fluid pressure within the catheter 122 at or near the catheter outlet 125, includes a compressible/expandable bellows 192 and a pair of metal plates 194 and 196 that are mounted on the ends of the bellows. The bellows 192, which may be formed from fiberglass or other suitable materials, is sealed and a vacuum is maintained within the internal space 198. The pressure sensor device 148c may be inserted into the catheter end 124, which is open prior to assembly, and secured in place with adhesive 166. Once the sensor device 148c is in place, the catheter end 124 may be thermal formed into a closed curved shape. Suitable adhesives include, but are not limited to, relatively soft adhesives such as silicone adhesive which results in soft, atraumatic tip. Radiopaque powder may be added to the adhesive 166 in order to insure that the catheter end 124 may be observed using a fluoroscope or the like.

Although the adhesive 166 fixes the position of metal plate 196 relative to the catheter 122, the bellows 192 and metal plate 194 (which faces upstream against the fluid flow direction) are free to move relative the catheter. This freedom allows the sensor device 148c to be in the expanded orientation illustrated in FIG. 14 when the pressure within the catheter 122 at or near the catheter outlet 125 is equal to physiological pressure (i.e. when there is no flow) and to be in a compressed orientation such as that illustrated in FIG. 15 when the catheter pressure is greater than physiological pressure (i.e. when there is flow F).

The exemplary sensor device 148c illustrated in FIGS. 14 and 15 is a "passive" device that is not powered, does not transmit data which is indicative of pressure and does not include a circuit board or antenna. Instead, the metal plates 194 and 196 form a capacitor and the capacitance of the capacitor varies with the distance between the plates, i.e. the capacitance decreases as the distance between the plates decreases. The capacitance of the capacitor defined by the metal plates 194 and 196 when the sensor device 148c is in the expanded orientation associated with a lack of flow (FIG. 14) will be a known value, and the capacitance will be less than the known value when the sensor device is compressed due to pressure within the catheter 122 that is higher than physiological pressure and indicative of fluid flow (FIG. 15). Accordingly, the interrogating device, e.g. the clinician's programming unit 200 or a patient's remote control (not shown), queries the sensor device 148c by simply measuring the capacitance of a circuit that includes the plates 194 and 196. The presence or absence of fluid flow at or near the catheter end 124 may be determined based on the measured capacitance.

Turning to FIGS. 16 and 17, the exemplary implantable infusion device 100 may be included in an infusion device system 10 that also includes a clinician's programming unit 200 which is not implanted in the patient. Alternative systems may include a patient's remote control (not shown), in place of or in addition to the clinician's programming unit, that is configured to determine whether or not fluid is flowing through the catheter outlet in the manner described below in the context of the clinician's programming unit. The exemplary clinician's programming unit 200 includes a housing 202, a touch screen display 204 (or other input device, such as a keypad, with or without a separate display), a battery or other power source 206, a controller 208, such as a microprocessor, microcontroller or other control circuitry, memory 210, and a communication device 212 (including an antenna if necessary). Although the present inventions are not limited to any particular communication device, the exemplary communication device 212 is a telemetry device that transmits an RF signal at a specified frequency. The RF signal may, in some instances, be a carrier signal that carries bit streams. The communication device 212 is configured to send signals to and receive signals from the communication device 132 in the implantable infusion device 100 by way of the antenna 134. Other exemplary communication devices include oscillating magnetic field communication devices, static magnetic field communication devices, optical communication devices, ultrasound communication devices and direct electrical communication devices. In some instances, the clinician's programming unit may also include an audible alarm 214.

Turning to communication with the sensor device 148 that measures a fluid flow characteristic at or near the catheter end 124, the exemplary clinician's programming unit 200 is also provided with a hand-held antenna 216. The antenna 216 includes an inductive coil 218, which is mounted within an annular member 220, and a handle 222. Additionally, although the antenna may 216 be an integral part of the clinician's programming unit 200, the exemplary antenna may be connected to (and disconnected from) the remainder of the programming unit by way of a cable 224 and connector 226. A patient's remote control may be configured so as to include the functionality of the antenna 216.

The exemplary clinician's programming unit 200 may be used to perform a variety of conventional control functions including, but not limited to, turning the infusion device ON or OFF and programming various infusion device parameters. Examples of such parameters include, but are not limited to, the rate of delivery of a given medication, the time at which delivery of a medication is to commence, and the time at which delivery of a medication is to end. Additionally, in at least some implementations, the implantable infusion device 100 will transmit signals to the clinician's programming unit 200. The signals provide status information about the infusion device 100 that may be stored in memory 210 and/or displayed on the display 204. Examples of such status information include, but are not limited to, the state of charge of the battery 126, the amount of medication remaining in the reservoir 110, and the amount of medication that has been delivered during a specified time period. The signals from the infusion device 100 may also be indicative of sensed physiological parameters in those instances where the infusion device is provided with physiological sensors (not shown).

The exemplary clinician's programming unit 200 illustrated in FIGS. 16 and 17 may, with the antenna 216 connected thereto, also be used to query the sensor device 148 to determine whether or not fluid is flowing through the catheter outlet 125. By way of example, but not limitation, the sensor device 148 and the clinician's programming unit 200 may be configured to operate in accordance with a standard RFID protocol at 13.56 MHz, which is suitable for penetrating body tissue. The clinician's programming unit 200 will transmit an electromagnetic field pulse to the sensor device 148 by way of the antenna 216. The electromagnetic energy supplied by the clinician's programming unit 200 resonates the antenna on the sensor device 148 (e.g. inductive coil 156 or inductive coil 180), which provides energy for the circuitry on the sensor device circuit board (e.g. circuit board 154 or circuit board 178) to perform the above-described fluid flow characteristic measurements and to generate a return signal. The return signal is picked up by the antenna 216, demodulated, and used by the programming unit 200 to provide the clinician with information regarding fluid flow. The information may be provided in visible form on the display 204 and/or may be provided in audible form with the alarm 214.

Alternatively, in those instances where the sensor device 148c is employed, the distance between the plates may be measured, either indirectly by measuring capacitance or directly through the use of fluoroscopy. Here too, the programming unit 200 will then provide the clinician with audible and/or visible information regarding fluid flow.

Another function that may be performed with the exemplary system 10 is locating the catheter outlet 125. The clinician's programming unit 200 may, for example, be used to evaluate the strength of the return signal from the sensor device 148 as the antenna 216 is being moved over the patient during a query. The antenna position at which the return signal from the sensor device 148 is maximized corresponds to the location of the sensor device. Here, the annular member 220 may be used as the crosshairs of the antenna 216. The location of the catheter outlet 125 may then be easily determined based on its known distance from the sensor device 148 (e.g. a few millimeters). A patient's remote control that includes the antenna functionality may also be used to located the catheter outlet 125.

Turning to FIG. 18, the system 10 may be used by a clinician in the following manner to determine the source of a therapeutic shortcoming associated with the implanted medical device 100. First, and frequently in response to a complaint by a patient, the clinician will query the sensor device 148 at or near the end 124 of implanted catheter 122 (Step 01). The clinician's programming unit 200 will, in response to the return signal or measured capacitance, determine whether or not there is fluid flow through the catheter outlet and provide the fluid flow information to the clinician (Step 02).

If there is flow through the catheter outlet 125, the clinician may assume that the implanted medical device 100 is functioning properly and that the source of the therapeutic shortcoming is related to the location of the catheter outlet or the effectiveness of the medication or other infusible substance. Here, the clinician's programming unit 200 may be used to determine the location of the sensor device 148 (and outlet 125) by evaluating the strength of the signal received by the antenna 216 as it is moved over the patient (Step 03). The actual location of the catheter outlet 125 may then be compared to the intended location. If the catheter outlet 125 is not in the intended location, then the catheter may be repositioned (Step 04). Alternatively, if the catheter outlet 125 is in the intended location, then the clinician may make an adjustment associated with the infusible substance itself, e.g. change the delivery rate or change to a different infusible substance (Step 05). The patient's reaction to the catheter 122 being repositioned or to the change associated with the infusible substance itself may then be evaluated (Step 06).

If, on the other hand, it is determined that there is no flow through the catheter outlet 125, the clinician may assume that the implanted medical device is not functioning properly. The pressure measured by the pressure sensor 144, which is located between the fluid transfer device 114 and the outlet port 118, may then be used to determine whether or not the catheter 122 is blocked or kinked (Step 07). More specifically, the pressure measured by the pressure sensor 144 is the pressure at the outlet port 118 and, if this pressure is higher than physiological pressure, a blocked or kinked catheter determination may be made (Step 08). The determination may be made by the clinician's programming unit 200, which may then provide an audible and/or visible indication that there is a catheter blockage or kink. Alternatively, or in addition, the clinician's programming unit 200 may provide an audible and/or visible indication of the pressure at the outlet port 118, which the clinician may use to make his/her own determination. Appropriate remedial steps, e.g. removing the blockage or replacing the catheter, may then be taken (Step 09).

Should, on the other hand, the pressure at an outlet port 118 that is connected to a catheter through which there is no flow at the outlet 125 be physiological pressure, it may be determined that there is a catheter leak, a catheter disconnect, a fluid transfer device failure, an empty reservoir, or the like (Step 10). The specific issue may then be determined by way of further investigation, e.g. querying the implanted medical device 100 to determine the fluid transfer device has failed or the reservoir is empty, or performing a dye study to determine whether there is a catheter leak or disconnect (Step 11).

It should also be noted here that, in some implementations, the sensor device 148 may be wirelessly queried by the controller 136 (e.g. by way of the communication device 132 and antenna 134) to, for example, periodically check for flow and alert the patient if there is a lack of flow. Alternatively, or in addition, in some implementations the results of a query of the pressure sensor 148 by the clinician's programming unit 200 (or a patient's remote control or other external device) may be provided to the controller 136 (e.g. by way of the communication device 132 and antenna 134).

Turning to FIGS. 19 and 20, the exemplary implanted medical device 100b illustrated therein is essentially identical to the implanted medical device 100. Here, however, the catheter 122b includes a plurality of flow sensor devices 148b along its length. Pressure sensors that permit fluid flow and/or combinations of such pressure sensors and flow sensors may be used in other implementations. Each flow sensor is configured to identify itself, as well as to transmit data that is representative of a fluid flow characteristic, when responding to a query. The use of sensor devices along the length of the catheter 122b allows the clinician to more accurately identify the source of problems. For example, if flow is sensed by one flow sensor 148b, and is not sensed by the flow sensor 148b immediately downstream, it may be assumed that there is a kink or tear in the catheter 122b between the flow sensors.

Although the inventions disclosed herein have been described in terms of the preferred embodiments above, numerous modifications and/or additions to the above-described preferred embodiments would be readily apparent to one skilled in the art. By way of example, but not limitation, the present inventions have application in infusion devices that include multiple reservoirs and/or outlets. It is intended that the scope of the present inventions extend to all such modifications and/or additions and that the scope of the present inventions is limited solely by the claims set forth below.

We claim:

1. An implantable infusion device, comprising:
   a housing;
   a fluid transfer device carried within the housing;
   a power supply carried within the housing and operably connected to the fluid transfer device;
   a catheter, including a outlet, operably connected to the fluid transfer device;
   a plurality of spaced sensor devices, which are not powered by the power supply within the housing, associated with the catheter and each configured to measure a within-the-catheter characteristic that is indicative of fluid flow through the catheter; and
   a controller, in communication with the plurality of spaced sensor devices, that identifies a location, relative to the plurality of spaced sensor devices, of a catheter blockage or leak based on the within-the-catheter characteristic measured by the plurality of spaced sensor devices.

2. An implantable infusion device as claimed in claim 1, wherein the fluid transfer device comprises an electromagnet pump.

3. An implantable infusion device as claimed in claim 1, wherein at least one of the sensor devices comprises a flow sensor device.

4. An implantable infusion device as claimed in claim 1, wherein the sensor devices include an antenna.

5. An implantable infusion device as claimed in claim 1, wherein the sensor devices comprise passive sensor devices.

6. An implantable infusion device as claimed in claim 1, wherein at least one of the sensor devices comprises a pressure sensor device.

7. An implantable infusion device as claimed in claim 1, wherein at least one of the sensor devices comprises a pressure sensor device and at least one of the sensor devices comprises a flow sensor.

8. A method of monitoring an infusion device that is implanted within a body and includes a reservoir for an infusible substance, a fluid transfer device, a catheter, and a plurality of spaced sensor devices associated with the catheter that each sense a within-the-catheter characteristic that is representative of fluid flow, the method comprising the steps of:

wirelessly querying at least two of the spaced sensor devices associated with the catheter that each sense the within-the-catheter characteristic that is representative of fluid flow; and identifying a location, relative to the at least two spaced sensors, of a catheter blockage or leak based on the result of the wireless query.

9. A method as claimed in claim 8, wherein the step of wirelessly querying the sensor devices comprises wirelessly querying the sensor devices associated with the catheter with a device that is external to the body.

10. A method as claimed in claim 8, further comprising the step of:

powering the sensor devices with the wireless query.

11. A method as claimed in claim 8, wherein at least one of the at least two of the spaced sensor devices comprises a pressure sensor.

12. A method as claimed in claim 8, wherein at least one of the at least two of the spaced sensor devices comprises a flow sensor.

13. A method as claimed in claim 8, wherein the at least two of the spaced sensor devices include a pressure sensor and a flow sensor.

14. A method of monitoring an infusion device that is implanted within a body and includes a reservoir for an infusible substance, a fluid transfer device, a catheter with an outlet through which fluid from the fluid transfer device flows into the body, and a sensor device that is located within the catheter at the catheter outlet and is configured to measure a characteristic that is indicative of fluid flow through the catheter outlet, the method comprising the step of:

measuring the characteristic that is indicative of fluid flow through the catheter outlet through which fluid from the fluid transfer device flows into the body with the sensor device that is located within the catheter at the catheter outlet through which fluid from the fluid transfer device flows into the body.

15. A method as claimed in claim 14, wherein the sensor device includes a pressure responsive element that senses a characteristic that is representative of pressure; and the step of measuring the characteristic that is indicative of fluid flow comprises measuring pressure at the sensor device.

16. A method as claimed in claim 14, wherein the sensor device includes an element that senses a characteristic that is representative of fluid flow; and the step of measuring the characteristic that is indicative of fluid flow comprises measuring flow with the sensor device.

17. A method as claimed in claim 14, wherein the catheter includes a closed distal end and the sensor device is located between the closed distal end and the outlet; and the step of measuring the characteristic that is indicative of fluid flow comprises measuring the characteristic that is indicative of fluid flow with the sensor device that is located within the catheter between the closed distal end and the outlet.

18. A method as claimed in claim 14, wherein the step of measuring the characteristic that is indicative of fluid flow comprises wirelessly querying the sensor device.

19. A method as claimed in claim 18, further comprising the step of:

powering the sensor device with the wireless query.

20. A method of monitoring an infusion device that is implanted within a body and includes a reservoir for an infusible substance, a fluid transfer device, a catheter with an outlet, and a pressure sensor, which includes a pressure responsive element that is located entirely within the catheter, the method comprising the steps of:

directly wirelessly querying the pressure sensor, which includes a pressure responsive element that is located entirely within the catheter, with a device that is external to the body; and powering the pressure sensor with the wireless query.

21. A method as claimed in claim 20, further comprising the step of:

determining whether fluid is flowing though the catheter outlet based on the result of the wireless query.

22. A method as claimed in claim 20, wherein the catheter is connected to an outlet port, the method further comprising the step of:

observing the pressure at the outlet port.

\* \* \* \* \*